United States Patent
Tyagi et al.

(10) Patent No.: US 8,350,030 B2
(45) Date of Patent: Jan. 8, 2013

(54) PROCESS FOR PRODUCING 5-FLUORO-1-(2R, 5S)-[2-(HYDROXYMETHYL)-1,3-OXATHIOLAN-5-YL]CYTOSINE

(75) Inventors: Om Dutt Tyagi, Jinnaram Mandal (IN); Umamaheswar Vasireddy Rao, Jinnaram Mandal, IN (US); Vellanki Sivarama Prasad, Jinnaram Mandal (IN); Arabinda Sahu, Jinnaram Mandal, IN (US)

(73) Assignee: Matrix Laboratories Limited, Secunderabad, Andhra Pradesh (IN)

( * ) Notice: Subject to any disclaimer, the term of this patent is extended or adjusted under 35 U.S.C. 154(b) by 234 days.

(21) Appl. No.: 12/746,739

(22) PCT Filed: Dec. 5, 2008

(86) PCT No.: PCT/IN2008/000814
§ 371 (c)(1),
(2), (4) Date: Jun. 7, 2010

(87) PCT Pub. No.: WO2009/084033
PCT Pub. Date: Jul. 9, 2009

(65) Prior Publication Data
US 2010/0256372 A1  Oct. 7, 2010

(30) Foreign Application Priority Data
Dec. 7, 2007 (IN) .......................... 2929/CHE/2007

(51) Int. Cl.
*C07D 411/04* (2006.01)
(52) U.S. Cl. .................................................. 544/317
(58) Field of Classification Search ................... 544/317
See application file for complete search history.

(56) References Cited

U.S. PATENT DOCUMENTS

| | | |
|---|---|---|
| 5,696,254 A | 12/1997 | Mansour et al. |
| 5,728,575 A | 3/1998 | Liotta et al. |
| 5,827,727 A | 10/1998 | Liotta et al. |
| 5,892,025 A | 4/1999 | Liotta et al. |
| 6,051,709 A | 4/2000 | Goodyear et al. |
| 2003/0013880 A1 | 1/2003 | Murthy et al. |

FOREIGN PATENT DOCUMENTS

| | | |
|---|---|---|
| EP | 0 515 157 A1 | 11/1992 |
| WO | WO 92/14743 | 9/1992 |
| WO | WO 20041085432 A1 | 10/2004 |

OTHER PUBLICATIONS

Ge et al., CAPLUS Abstract 148:11436 (2007).*
Santosh Richhariya, et al "Process for the Purification of Nucleoside Analogue" IP.Com Journal, IPCOM000144028D Dec. 14, 2006.

* cited by examiner

Primary Examiner — Deepak Rao
(74) Attorney, Agent, or Firm — Workman Nydegger

(57) ABSTRACT

Disclosed herein an improved process for producing 5-Fluoro-1-(2R,5S)-[2-(hydroxymethyl)-1,3-oxathiolan-5-yl]cytosine and its pharmaceutical acceptable salts.

12 Claims, 1 Drawing Sheet

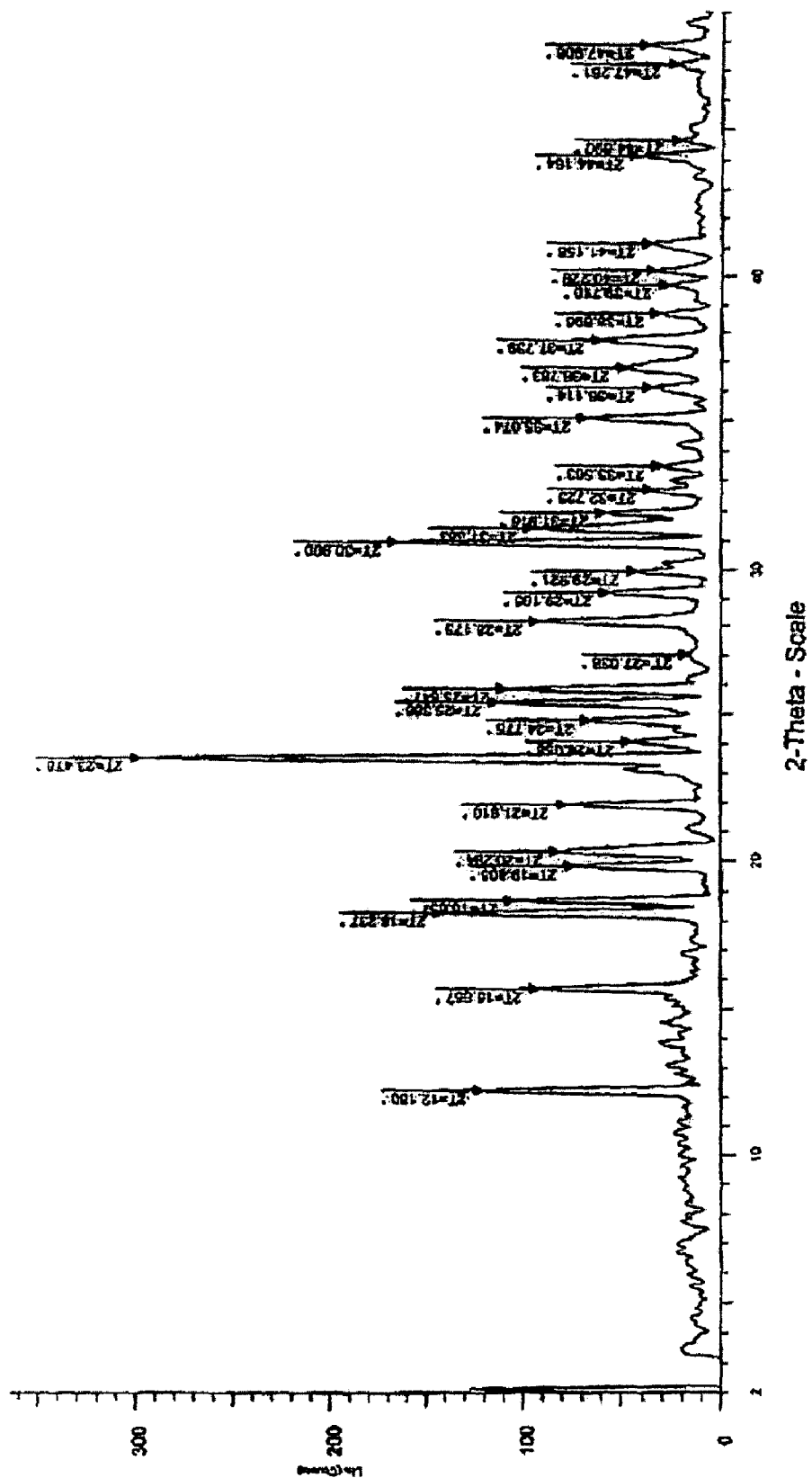

PROCESS FOR PRODUCING 5-FLUORO-1-(2R, 5S)-[2-(HYDROXYMETHYL)-1,3-OXATHIOLAN-5-YL]CYTOSINE

This application is a 371 of PCT/IN08/00814 filed Dec. 5, 2008.

FIELD OF THE INVENTION

The present invention relates to an improved process for producing 5-Fluoro-1-(2R,5S)-[2-(hydroxymethyl)-1,3-oxathiolan-5-yl]cytosine and its pharmaceutically acceptable salts.

BACKGROUND OF THE INVENTION

5-Fluoro-1-(2R,5S)-[2-(hydroxymethyl)-1,3-oxathiolan-5-yl]cytosine (Emtricitabine) is used as an antiviral drug. Emtricitabine is marketed under the trade name Emtriva. Emtricitabine is the (−) enantiomer of a thio analogs differing from other cytosine analogs viz. Lamivudine in that it has a fluorine in the 5-position.

There are various processes used in the prior art for preparation of Emtricitabine using different synthetic routes.

WO 92/14743 discloses the racemic mixture of cis isomers, which are prepared using standard reactions followed by resolution employing enzymatic methods to yield 2R, 5S enantiomer.

Stereoselective synthetic routes were subsequently developed, which by means of the use of chiral auxiliaries such as menthol, allow the desired stereochemistry to be induced and allow Emtricitabine to be obtained directly as single enantiomer. U.S. Pat. No. 5,696,254 illustrates stereoselective synthesis approach for synthesis of Emtricitabine, as shown below:

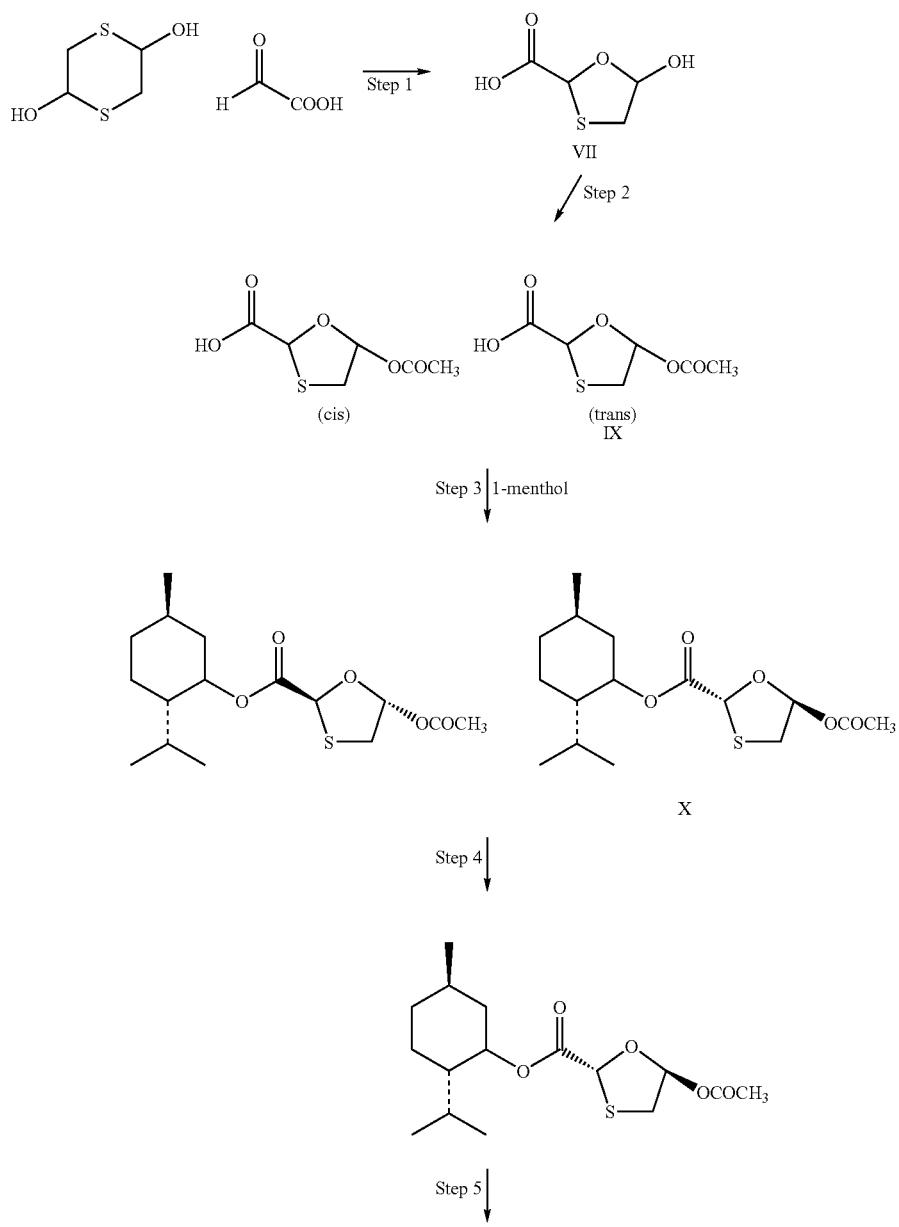

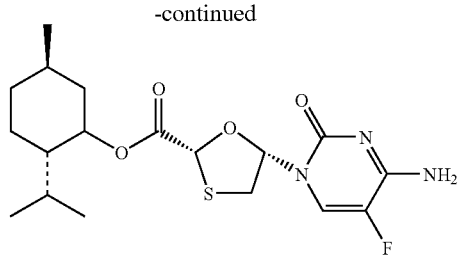

XI

Step 6 ↓

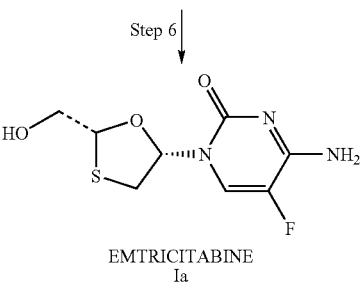

EMTRICITABINE
Ia

In the above scheme the trans oxathiolane is prepared (Step 1, VIII) which, when acetylated (Step 2, IX) and condensed with 1-menthol, leads to the mixture of intermediate diastereoisomers (Step 3, X). The desired diastereomer is isolated by fractional crystallization (Step 4) and coupled with silylated 5-fluorocytosine (III) (Step 5), leading to the derivative XI which finally by reductive removal of the chiral auxiliary (Step 6) gives Emtricitabine.

U.S. Pat. No. 6,051,709 describes a stereoselective process for the synthesis of cis nucleosides, this process differing from the above process essentially by the use of leaving groups other than acetate such as halo, cyano or sulphonate in the coupling reaction of the intermediate X with the activated 5-fluorocytosine III.

However, the experimental illustration is limited to the preparation of the non-fluoro analogue of Emtricitabine, known as Lamivudine (as illustrated in scheme 1, columns 9-10), without any indication regarding the actual process yields. Example 1 describes the preparation of 5-hydroxyoxathiolane required by reacting 1-menthyl glyoxalate and dithianediol (part a, column 10), and the subsequent formation of the chloro derivative (part b, column 10) and its coupling reaction with cytosine silylate (last paragraph, column 10, first paragraph, column 11). The resulting product, which precipitates from the reaction medium, is recovered by simple filtration and subjected to reductive removal of the chiral auxiliary to give the crude Lamivudine, which is purified, not by direct crystallization of the base but of the salified form, in particular of the salicylate. It is obvious that, by this procedure, a subsequent basic treatment will be necessary to release the lamivudine base from its salt. This procedure, which does not appear to present any particular implementation difficulties in the case of Lamivudine, becomes entirely inapplicable when used for the preparation of Emtricitabine.

U.S. Pat. No. 5,728,575 disclose a method to obtain Lamivudine and Emtricitabine via enzymatic resolution of the 5'-acyl protected racemic nucleoside using pig liver esterase, porcine pancreatic lipase, or subtilisin.

U.S. Pat. No. 5,827,727 disclose a method to obtain Lamivudine and Emtricitabine via stereoselective deamination using cytidine deaminase.

U.S. Pat. No. 5,892,025 disclose a method for the resolution of the combination of the enantiomers of cis-Emtricitabine by passing the cis-Emtricitabine through an acetylated β-cyclodextrin chiral column.

The present invention provides an alternative process stereo-selective preparation of Emtricitabine, which is commercially viable and allows the desired product, to be obtained in good yield.

SUMMARY OF THE INVENTION

It is a principal object of the present invention to provide an improved process for producing 5-Fluoro-1-(2R,5S)-[2-(hydroxymethyl)-1,3-oxathiolan-5-yl]cytosine and its pharmaceutical acceptable salts, wherein the process avoids the drawback associated in the prior art process.

It is another object of the present invention to provide an improved process for producing 5-Fluoro-1-(2R,5S)[2-(hydroxymethyl)-1,3-oxathiolan-5-yl]cytosine and its pharmaceutical acceptable salts in high yield without using any chromatographic technique.

This and other objectives of the present invention are further attained and supported by the following embodiments described herein. However, the scope of the invention is not restricted to the described embodiments herein after.

In accordance with one preferred embodiment of the present invention, there is provided a process for producing 5-Fluoro-1-(2R,5S)[2-(hydroxymethyl)-1,3-oxathiolan-5-yl]cytosine of Formula I, wherein the process comprises of reducing the compound (2R,5S)-5-(4-Amino-5-fluoro-2-oxo-2H pyrimidin-1-yl)-[1,3]-oxathiolane-2-carboxylic acid, 2S-isopropyl-5R-methyl-1R-cyclohexyl Ester) of Formula II to obtain compound (2R-Cis)-2-hydroxymethyl-5-(5'fluoro cytosine-1'-yl)-1,3-oxathiolane of Formula III, followed by in_situ salification of compound (2R-Cis)-2- hydroxymethyl-5-(5'fluoro cytosine-1'-yl)-1,3-oxathiolane of Formula III employing an organic or mineral acid in an organic solvent to obtain compound (2R-Cis)-2-hydroxymethyl-5-(5'fluoro cytosine-1'-yl)-1,3-oxathiolane hydrochloride of Formula IV, neutralizing the resultant compound (2R-Cis)-2-hydroxymethyl-5-(5'fluoro cytosine-1'-yl)-1,3-oxathiolane hydrochloride of Formula IV employing an organic solvent in presence of organic amine bases to obtain 5-Fluoro-1-(2R,5S)-[2-(hydroxymethyl)-1,3-oxathiolan-5-yl]cytosine of Formula I.

In accordance with another preferred embodiment of the present invention, there is provided a process for producing 5-Fluoro-1-(2R,5S)-[2-(hydroxymethyl)-1,3-oxathiolan-5-yl]cytosine of Formula I, wherein the reduction and salification reactions are performed in a single pot.

DETAILED DESCRIPTION OF THE INVENTION

While this specification concludes with claims particularly pointing out and distinctly claiming that, which is regarded as the invention, it is anticipated that the invention can be more readily understood through reading the following detailed description of the invention and study of the included examples.

The present invention provides an improved process for producing 5-Fluoro-1-(2R,5S)-[2-(hydroxymethyl)-1,3-oxathiolan-5-yl]cytosine of Formula I, and its pharmaceutically acceptable salts thereof, Formula I

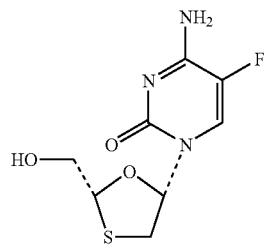

the process comprises the steps of:
a) reducing the compound (2R,5S)-5-(4-Amino-5-fluoro-2-oxo-2H pyrimidin-1-yl)-[1,3]-oxathiolane-2-carboxylic acid, 2S-isopropyl-5R-methyl-1R-cyclohexyl Ester) of Formula II employing a reducing agent;

Formula II

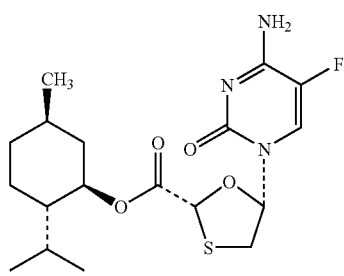

to obtain compound (2R-Cis)-2-hydroxymethyl-5-(5'fluoro cytosine-1'-yl)-1,3-oxathiolane of Formula III;

Formula III

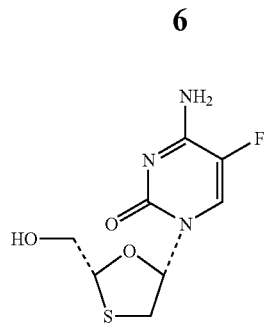

b) followed by in_situ salification of compound (2R-Cis)-2-hydroxymethyl-5-(5'fluoro cytosine-1'-yl)-1,3-oxathiolane of Formula III employing an organic or mineral acid in an organic solvent to obtain the compound of Formula IV;

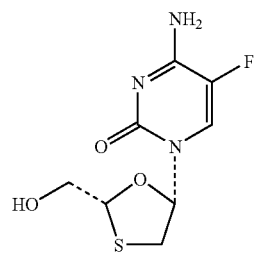

wherein X is organic acid or mineral acid
Formula IV c) neutralizing the compound (2R-Cis)-2-hydroxymethyl-5-(5'fluoro cytosine-1'-yl)-1,3-)-oxathiolane hydrochloride of Formula IV employing an organic solvent in presence of an organic amine base to obtain compound of Formula I.

According to the present invention, the reduction of compound of Formula II is performed by dissolving said compound in alcohol and the reaction mass is cooled and a solution of sodium borohydride in 0.12 N sodium hydroxide solution is added to the resultant. After completion of the reaction, as monitored by TLC, the pH of the reaction mass is adjusted to 6.0-6.5. The obtained thick mass is dissolved in isopropanol and the reaction mixture is refluxed. The reaction mixture is filtered to remove insolubles. The crude reaction mass is salified with organic or mineral acid in an alcoholic solvent. By the addition of organic or mineral acid, precipitation occurs and the obtained wet mass is cooled. The reaction mass is filtered whereby white to light brown solid is obtained as salt.

The salification of compound of Formula III according to the process is carried out in alcoholic solvents like methanol, ethanol or isopropyl alcohol or mixtures thereof. The organic or mineral acid is selected from hydrochloric acid, hydrobromic acid and methane sulfonic acid or mixtures thereof, preferably hydrochloric acid.

BRIEF DESCRIPTION OF DRAWING

The compound of Formula IV is obtained as a crystalline solid having the PXRD pattern as shown in FIG. 1.

The salt of compound of Formula IV is subjected to standard basic treatment to give Emtricitabine of Formula I as highly pure compound. The hydrochloride salt of compound of Formula IV is neutralized in a suitable solvent in the presence of a suitable base. Neutralization can be affected in alcohols and chlorinated solvents or mixtures thereof. Typically the compound of Formula IV is dissolved in methanol and triethylamine is added to the solution. The reaction mixture is refluxed and the solvent distilled off. The obtained mass is cooled and to this methylene chloride is added again and refluxed. The reaction mass is cooled to 25-35° C. for 1 hr. The solid obtained is collected by filtration and leached with methylene chloride. The obtained solid is dried to give highly pure Emtricitabine.

The compound of Formula II can be prepared by processes known in the art such as for example EP 515157, U.S. Pat. No. 6,051,709 and WO 04/085432.

In the present invention both the reduction and salification reactions are performed in one-pot only.

In the process of the present invention stereoselective preparation of Emtricitabine allows the desired product to obtain in high yield at least 75%, preferably at least 80%, Further the use of chromatographic techniques is also avoided in the present invention, which are particularly disadvantageous from a practical point of view.

Powder X-Ray Diffraction (PXRD)

The said compound of formula IV of the present invention is characterized by their X-ray powder diffraction pattern. Thus, the X-ray diffraction patterns of said compound of formula IV of the invention were measured on PANalytical, X'Pert PRO powder diffractometer equipped with goniometer of θ/θ configuration and X'Celerator detector. The Cu-anode X-ray tube was operated at 40 kV and 30 mA. The experiments were conducted over the 2θ range of 2.0°-50.0°, 0.030° step size and 50 seconds step time.

The examples that follow are not intended to limit the scope of the invention as defined hereinabove or as claimed below:

Example-1

Preparation of (2R,5S)-5-(4-Amino-5-fluoro-2-oxo-2H-pyrimidin-1-yl)-[1,3]-oxathiolane-2-carboxylic acid, 2S-isopropyl-5R-methyl-1R-cyclohexyl ester Methylene chloride (450 ml) and methane sulfonic acid (0.80 g) was charged and the solution was cooled to 20° C. (2R,5R)-5-Hydroxy-[1,3]-oxathiolane-2-carboxylic acid, 2S-isopropyl-5R-methyl-1R-cyclohexyl ester (100 g) was charged at 20° C. To this solution dimethyl formamide (28 g) was added. The solution was further cooled to 8° C. Thionyl chloride (44 g) was added drop wise at 8-10° C. The temperature of the reaction mass was maintained at, 10-15° C. for 4 hrs. The reaction mass was heated to reflux and maintained at reflux temperature for 4 hrs. Methylene chloride was distilled at atmospheric pressure up to residual volume of 300 ml-350 ml 5-Fluorocytosine (45 g) was dissolved in toluene (120 ml) and subsequently hexamethyldisilazane (65.4 g) and methane sulfonic acid (0.4 g) were added. The entire reaction mass was heated to reflux and maintained for 5 hrs. 40 ml toluene was distilled at atmospheric pressure. The reaction mass was cooled to 65° C. and triethylamine (35.5 g) was added at 65° C. The reaction mass was cooled to 60° C. and the above residue was added drop wise at 55-65° C. Temperature was maintained at mild reflux (53-56° C.) for 5 hrs. The reaction was monitored by HPLC and then reaction mass was cooled to 35° C. The above reaction mass was added to a mixture of water (600 ml) and triethylamine (24.5 g) during at 25-35° C. The reaction mass was stirred for 1 hr at 25-35° C. pH of the mass was adjusted to 7.8 with triethylamine. The organic layer was separated and solvent was distilled under vacuum completely to give thick residue and a mixture of n-hexane (450 ml) and ethylacetate (50 ml) were added. The suspension was heated to reflux and maintained at reflux temperature for 2 hrs. The mass was slowly cooled to 25-35° C. Stirring was maintained for 10 hrs at 25-35° C. Off white to light brown solid is filtered and washed with water.

Wet cake was suspended in a mixture of water (200 ml), hexane (100 ml) and ethylacetate (100 ml). The suspension was stirred for 1 hr at 25-35° C. and filtered, washed with water (200 ml). Solid was dried at 60-65° C. to give 78 gm.

Example-2

Preparation of (2R-Cis)-2-hydroxy methyl-5-(5'-fluorocytosin-1'-yl)-1,3-oxathiolane hydrochloride A solution of dipotassium hydrogen phosphate (137 g) in water (330 ml) was stirred for 10 mins. Ethanol (900 ml) was added and the mass was cooled to 18° C. (2R,5S)-5-(4-Amino-5-fluoro-2-oxo-2H-pyrimidin-1-yl)-[1,3]-oxathiolane-2-carboxylic acid, 2S-isopropyl-5R-methyl-1R-cyclohexyl ester (100 gm} was added at 15-20° C. The suspension was stirred for 1 hr at 18-20° C. A solution of sodium borohydride [(20 gm) in 0.12 N Sodium hydroxide solution (95 ml)] was added dropwise maintaining the temperature at 18-20° C. The mixture was stirred at 18-22° C. for 4 hrs. On completion of the reaction as confirmed by TLC, the reaction mass was transferred into a separating funnel and the layers were separated. pH of organic layer was adjusted to 6.0-6.5 with 6 N HCl (~13 ml) and again adjusted to pH 8.0 to 8.5 with 2N Sodium hydroxide. Reaction mass was transferred and distilled at atmospheric pressure to ~250 ml residual volume. Residue was cooled to 25-35° C. Menthol was extracted with toluene. Aqueous solution is decolourised with activated carbon (5 gm) and filter bed is washed with water (100 ml). Water is distilled under vacuum at 45-55° C. to thick mass. Residual moisture was recovered by co-distillation with isopropanol. Finally thick mass was dissolved in isopropanol (500 ml) by heating to reflux and maintaining for 30 mins. The isopropanol solution was cooled to 25-35° C. A solution of IPA. HCl (75 gms ~15% w/w) was added during at 25-35° C. The suspension of hydrochloride salt was maintained for 1 hr at 25-5° C. The mass was cooled to 0° C. and stirred for 2 hrs at 0-5° C. The off white to light brown solid is collected by filtration and solid was washed with chilled isopropanol (50 ml) The product is dried at 50-55° C. to give 59 gm off white-light brown coloured HCl salt.

Example-3

Preparation of Emtricitabine

Emtricitabine hydrochloride (100 g) was dissolved in methanol (500 ml). The mixture was stirred for 15 mins.

Triethylamine (80 g) was added to the solution at 25-35° C. The solution was heated to reflux and maintained at reflux temperature 60-65° C. for 60 mins. The reaction mass was cooled to 25-35° C. and decolourised with activated carbon at 25-35° C. Filtrate was distilled under vacuum to thick residue below 50° C. The mass was cooled to 25-35° C. Traces of methanol was removed by flushing with methylene chloride (100 ml). Methylene chloride was charged to the residue and heated to reflux. Reaction mass was maintained at reflux temperature for 2 hrs. The suspension was cooled to 25° C. The reaction mass was maintained at 25-35° C. for 1 hr. Solid was collected by filtration and leached with methylene chloride (200 ml) and washed with methylene chloride (100 ml). The solid was dried at 45-50° C. to get Emtricitabine (67 gm, 82%). This technical grade Emtricitabine can be decolourised in IPA to get pharmaceutically accepted quality product While this invention has been described in detail with reference to certain preferred embodiments, it should be appreciated that the present invention is not limited to those precise embodiments. Rather, in view of the present disclosure, which describes the current best mode for practicing the invention, many modifications and variations would present themselves to those skilled in the art without departing from the scope and spirit of this invention.

We claim:

1. An improved process for producing 5-Fluoro-1-(2R,5S)-[2-(hydroxymethyl)-1,3-oxathiolan-5-yl]cytosine of Formula I and its pharmaceutically acceptable salts,

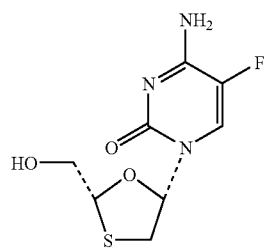

Formula I the process comprising the steps of:
  a. reducing the compound (2R,5S)-5-(4-Amino-5-fluoro-2-oxo-2H pyrimidin-1-yl)-[1,3]-oxathiolane-2-carboxylic acid, 2S-isopropyl-5R-methyl-1R-cyclohexyl Ester) of Formula II employing a reducing agent;

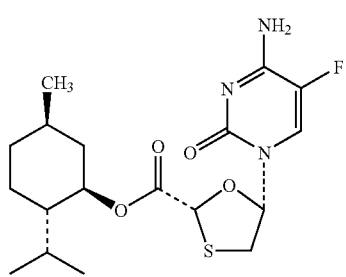

Formula II to obtain the compound (2R-Cis)-2-hydroxymethyl-5-(5 fluoro cytosine-yl)-1,3-oxathiolane of Formula III;

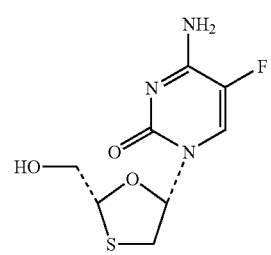

Formula III b. followed by in_situ salification of compound (2R-Cis)-2-hydroxymethyl-5-(5'fluoro cytosine-1'-yl)-1, 3-oxathiolane of Formula III employing a mineral acid or sulfonic acid in presence of an organic solvent to give compound (2R-Cis)-2-hydroxymethyl-5-(5'fluoro cytosine-1'-yl)-1,3-oxathiolane salt of Formula IV,

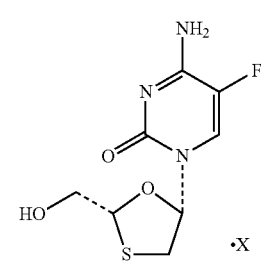

Formula IV wherein X is mineral acid or sulfonic acid; and
  c. neutralizing the compound of Formula IV employing an organic solvent in presence of an organic amine base to obtain 5-Fluoro-1-(2R,5S)-[2-(hydroxymethyl)-1,3-oxathiolan-5-yl]cytosine of Formula I.

2. The process according to claim 1, wherein the reducing agent is sodium borohydride.

3. The process according to claim 1, wherein the organic solvent used in step (b) is selected from alcohols.

4. The process according to claim 3, wherein the alcohol is selected from methanol, isopropanol or mixtures thereof.

5. The process according to claim 1, wherein the mineral acid or sulfonic acid is selected from hydrochloric acid, hydrobromic acid and methane sulfonic acid.

6. The process according to claim 5, wherein the mineral acid is hydrochloric acid.

7. The process according to claim 1, wherein the organic solvent used in step (c) is selected from alcohols and chlorinated solvents or mixtures thereof.

8. The process according to claim 7, wherein the organic solvent is selected from methanol, methylene chloride and chloroform.

9. The process according to claim 1, wherein the organic amine bases is selected form triethylamine, and N,N-diisopropylethylamine.

10. The Process according to claim 1, wherein compound of Formula IV is (2R-Cis)-2-hydroxymethyl-5-(5 fluorocytosine-1-yl)-1,3-oxathiolane hydrochloride.

11. An improved process for producing 5-Fluoro-1-(2R, 5S)-[2-(hydroxymethyl)-1,3-oxathiolan-5-yl]cytosine of Formula I and its pharmaceutically acceptable salts,

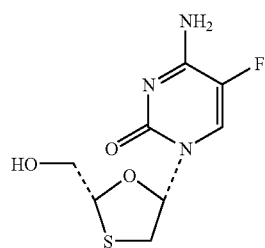

Formula I the process comprising the steps of:
a. reducing the compound (2R,5S)-5-(4-Amino-5-fluoro-2-oxo-2H pyrimidin-1-yl)-[1,3]-oxathiolane-2-carboxylic acid, 2S-isopropyl-5R-methyl-1R-cyclohexyl Ester) of Formula II employing a reducing agent;

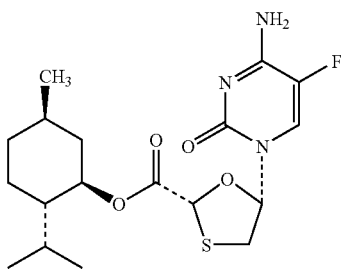

Formula II to obtain the compound (2R-Cis)-2-hydroxymethyl-5-(5'fluoro cytosine-yl)-1,3-oxathiolane of Formula III;

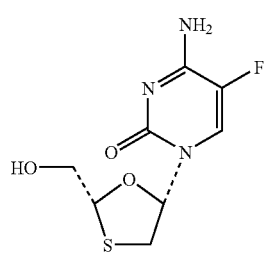

Formula III b. followed by in_situ salification of compound (2R-Cis)-2-hydroxymethyl-5-(5'fluoro cytosine-1'-yl)-1,3-oxathiolane of Formula III employing a mineral acid in presence of an organic solvent to give compound (2R-Cis)-2-hydroxymethyl-5-(5'fluoro cytosine-1'-yl)-1,3-oxathiolane salt of Formula IV,

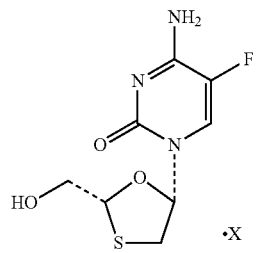

Formula IV wherein X is organic acid or mineral acid; and c. neutralizing the compound of Formula IV employing an organic solvent in presence of an organic amine base to obtain 5-Fluoro-1-(2R,5S)-[2-(hydroxymethyl)-1,3-oxathiolan-5-yl]cytosine of Formula I.

12. An improved process for producing 5-Fluoro-1-(2R, 5S)-[2-(hydroxymethyl)-1,3-oxathiolan-5-yl]cytosine of Formula I and its pharmaceutically acceptable salts,

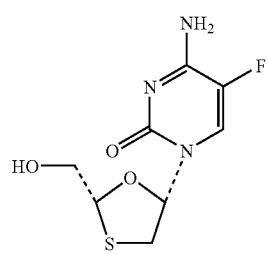

Formula I the process comprising the steps of:
a. reducing the compound (2R,5S)-5-(4-Amino-5-fluoro-2-oxo-2H pyrimidin-1-yl)-[1,3]-oxathiolane-2-carboxylic acid, 2S-isopropyl-5R-methyl-1R-cyclohexyl Ester) of Formula II employing a reducing agent;

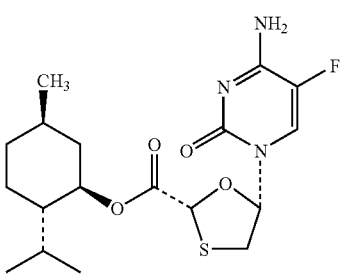

Formula II to obtain the compound (2R-Cis)-2-hydroxymethyl-5-(5'fluoro cytosine-yl)-1,3-oxathiolane of Formula III;

13

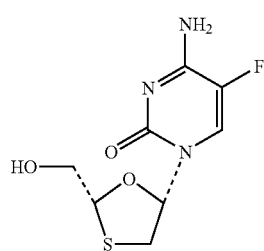

Formula III b. followed by in_situ salification of compound (2R-Cis)-2-hydroxymethyl-5-(5'fluoro cytosine-1'-yl)-1,3-oxathiolane of Formula III employing an organic acid or mineral acid in presence of an organic solvent to give compound (2R-Cis)-2-hydroxymethyl-5-(5'fluoro cytosine-1'-yl)-1,3-oxathiolane salt of Formula IV;

14

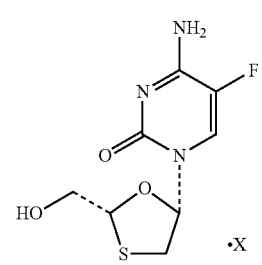

Formula IV wherein X is organic acid or mineral acid; and c. neutralizing the compound of Formula IV employing an organic solvent in presence of an organic amine base to obtain 5-Fluoro-1-(2R,5S)-[2-(hydroxymethyl)-1,3-oxathiolan-5-yl]cytosine of Formula I.

* * * * *